US005807551A

United States Patent [19]

Reynolds

[11] Patent Number: 5,807,551
[45] Date of Patent: Sep. 15, 1998

[54] METHOD TO PROVIDE ARTIFICIAL PASSIVE IMMUNITY IN BIRDS

[75] Inventor: Donald L. Reynolds, Ames, Iowa

[73] Assignee: Iowa State University Research Foundation, Inc., Ames, Iowa

[21] Appl. No.: 697,219

[22] Filed: Aug. 21, 1996

Related U.S. Application Data

[60] Provisional application No. 60/014,478 Apr. 1, 1996.

[51] Int. Cl.[6] ........................ A61K 39/42; A61K 39/395; A61K 39/40; A61K 35/44

[52] U.S. Cl. .................................... 424/159.1; 424/157.1; 424/130.1; 424/169.1; 424/581; 800/2

[58] Field of Search .............................. 426/614; 119/46, 119/6.8; 424/130.1, 184.1, 157.1, 159.1, 169.1, 581; 800/2, DIG. 5, DIG. 6

[56] References Cited

U.S. PATENT DOCUMENTS

| | | | |
|---|---|---|---|
| 4,458,630 | 7/1984 | Sharma et al. | 119/1 |
| 4,710,377 | 12/1987 | Schenkel et al. | 424/88 |
| 4,748,018 | 5/1988 | Stolle et al. | 424/87 |
| 5,136,979 | 8/1992 | Paul et al. | 119/6.8 |
| 5,367,054 | 11/1994 | Lee | 530/359 |
| 5,397,569 | 3/1995 | Whitfill et al. | 424/178.1 |
| 5,420,253 | 5/1995 | Emery et al. | 530/423 |
| 5,438,954 | 8/1995 | Phelps et al. | 119/6.8 |

FOREIGN PATENT DOCUMENTS

| | | | |
|---|---|---|---|
| WO 94/06904 | 3/1994 | WIPO | 424/204.1 |
| WO 95/03813 | 2/1995 | WIPO | 424/130.1 |

OTHER PUBLICATIONS

Banushali et al., Poultry Science, 73–1158–61 (1994).
McKinney et al., J. Immunol. Methods, 96:271–78 (1987).
Naveh et al., Proc. 41st Western Poultry Disease Conference, pp. 27–28 (1992).
Sharma et al., Avian Diseases, 26:134–149 (1982).
Stone et al., Avian Diseases, 36:1048–1051 (1992).
Vasington et al., Poultry Science, 39:1418–1427 (1960).
Wills et al., Avian Diseases, 7:5–12 (1963).
Tizard, Veterinary Immunology, W. B. Saunders Co., ISBN 0–7216–8868–3. pp. 215–216 and 226, 1977.
Fahey et al, Antibody to the 32K structural protein of infectious bursal disease virus neutralizes viral infectivity in vitro and confers protections on young chickens, J. Gen. Virol., vol. 66 No. 12 pp. 2693–2702, 1985.
Avakian et al, Efficacy of a Novel Infectious Bursal Disease Vaccine Administered IN Ovo to Broiler Chickens, Poult. Sci., vol. 72, Suppl. 1, p. 49 #147, 1993.
Steinbuch et al, Antibody Purification using caprylic acid, Antibodies: A Laboratory Manual, Cold Spring Harbor Publications, p. 300, 1988.

Fahey et al, Virus–neutralizing and passively protective monoclonal antibodies to infectious bursal disease virus of chickens, Avian Diseases, vol. 35, No. 2, pp. 365–373, 1991.

*Primary Examiner*—Jasemine C. Chambers
*Assistant Examiner*—Deborah J. R. Clark
*Attorney, Agent, or Firm*—Fish & Richardson, P.C., P.A.

[57] ABSTRACT

The invention provides methods for inducing long-term passive immunity in birds, through administration of superconcentrated antibodies to hatching eggs or to post-hatch birds. The superconcentrated antibodies may originate from any source, including avian or mammalian species, and are specific for one or more disease agents against which passive protection is desired.

17 Claims, No Drawings

METHOD TO PROVIDE ARTIFICIAL PASSIVE IMMUNITY IN BIRDS

CROSS REFERENCE TO RELATED APPLICATIONS

This application claims benefit from U.S. provisional patent application Ser. No. 60/014,478, filed Apr. 1, 1996.

BACKGROUND OF THE INVENTION

This invention relates to animal disease protection, and in particular to induction of passive immunity in avian species.

It is a widely accepted practice to vaccinate poultry for protection against various diseases including Newcastle disease (ND), infectious bronchitis and infectious bursal disease. Broiler chickens are commonly coarse-spray vaccinated at the hatchery, even though the birds may possess maternally derived antibody. The rationale for this practice is that the vaccine is beneficial in inducing a local immune response even though maternal antibodies generally interfere with the systemic response (as measured by serologic antibody). Additionally, broiler chickens generally are provided a "booster" vaccination between 2–4 weeks of age to induce protective immunity. The booster vaccination is a serious economic consideration for the producer. If the booster is administered too early, then residual maternal antibodies may interfere and result in inadequate protection. If the booster vaccination is administered too late, then the flock is susceptible to infection. Unfortunately, there is great variation between birds within a flock with respect to maternal antibody levels. Thus, the "art" of vaccinating a flock is reduced to fortuitous timing.

Perhaps the greatest concern regarding booster vaccinating a broiler flock is the biological consequences of vaccination. That is, the vaccine stimulates the immune response and in so doing has a negative impact on the performance parameters of the birds. This is generally referred to by poultry personnel as the "vaccine reaction". Some vaccines, such as infectious bursal disease vaccines, can cause immunosuppression and may make the bird more susceptible to other infections. Vaccine reactions are serious deterrents to the use of conventional vaccines. Additionally, the use of live vaccines increases the likelihood of perpetuating the disease by generating new strains of disease agents. As a consequence, live vaccines are not well suited to disease eradication programs.

Investigations in the 1960's provided evidence that antibody can be administered to chickens in order to provide protection against Newcastle disease (ND). Such protection of subject animals afforded by administered antibody is termed "passive immunity," since the subject animal is the passive recipient of protective antibodies. Nevertheless, the immune system of the recipient generally continues to play a variety of roles in the over-all immune response engendered by the administered antibody.

The advantages of passive immunization over traditional methods of vaccinating chickens with inactivated and/or live conventional vaccines include: (1) passive immunity protects without the stress induced by active immunity, e.g., stress induced by a vaccine reaction; (2) passive immunity employs no live agents, thus decreasing the likelihood of perpetuating disease and giving rise to new disease agents, for example recombinant variant strains derived from vaccine and field strains; (3) passive immunity augments, rather than antagonizes, maternal immunity; (4) passive immunity provides protection immediately upon administration; (5) passive immunity can be induced against many different types of disease-causing agents simultaneously without adverse effects.

Although the potential advantages of passive immunity are clear, to date a number of shortcomings are apparent. These include (1) relatively short duration of immunity, commonly 1–2 weeks and generally less than 4 weeks; (2) requirements for large volumes of antibody preparation (i.e. greater than 1 ml). For passive immunity to be commercially feasible in broiler chickens, protection must extend for the duration of the grow-out period, typically 4–8 weeks. If birds were to be administered passive antibody in a commercially viable setting, the antibody would need to be administered in accordance with industry practices, either by in ovo injection of hatching eggs or by parenteral (e.g., subcutaneous) injection of day-old chicks. The volume of antibody preparation to be injected in ovo generally is in the range of 0.05–0.20 ml and for parenteral injection generally should not exceed 0.5 ml. For older birds (more than one day post-hatch), larger volumes may be appropriate.

In regards to in ovo vaccination, the current state of the art applies to vaccinating hatching eggs with live agent vaccines in which the embryo induces an active immunity. Sharma and Burmester, *Avian Diseases* 26:134–149 (1982) and U.S. Pat. No. 4,458,630, demonstrated the efficacy of vaccinating live agents in ovo. Their work demonstrated the feasibility of vaccinating birds with live infectious agents prior to hatch. On the other hand, in ovo administration in conjunction with passive protection has not been reported.

SUMMARY OF THE INVENTION

The invention includes a method for providing artificial passive immunity in an avian species by administering a preparation of antibody to an egg. The term "egg" as used herein refers to the shelled structure laid by a member of an avian species. Thus, an "egg" includes, initially, the egg yolk (the actual "egg" of an avian species), egg white, shell membranes, calcium carbonate shell and other associated structures. The term "egg" also includes all developmental stages of the embryo up to the time of hatching. The antibody is administered in an amount effective to provide, to the egg or to a bird derived from the egg, long-term passive protection from a disease agent.

Preferably the disease agent is one that engenders natural passive immunity, i.e., a virus or other disease agent that causes production of protective antibody in the mother that is passed into the developing embryo within the egg prior to laying. Such disease agents include but are not limited to Newcastle disease virus and infectious bursal disease virus. Protection from other disease agents, including those that do not generally lead to natural passive immunity in the developing embryo, may also be accomplished by the methods of the present invention. For example, the methods are generally applicable to any disease agent against which neutralizing antibodies can be generated.

The eggs may be of any avian species, for example *Gallus gallus* (chickens). If the eggs are those of chickens, the eggs may be designated for production of broiler chickens. The antibodies to be administered may originate from any source, including avian or mammalian species, and the antibodies may be superconcentrated as described below. The invention also includes eggs treated as described above with exogenous antibody. By "exogenous" is meant antibody that originates outside the egg.

In a further aspect of the invention, post-hatch birds are parenterally administered a preparation of superconcentrated antibody, in an amount effective to provide long-term passive protection from a disease agent. As described above for treatment of eggs, the disease agent preferably engenders natural passive immunity, for example Newcastle Disease Virus or infectious bursal disease virus. Nevertheless, other disease agents are also treatable with the methods of the present invention.

The superconcentrated antibody preparation may be administered to birds of various avian species, including *Gallus gallus*, and specifically including broiler chickens. Preferably the preparation of superconcentrated antibody is administered by subcutaneous injection. As with administration to eggs, the antibodies administered to post-hatch birds may originate from any source, including avian or mammalian species, so long as the antibodies are effective against the disease agent or agents desired to be targeted. The invention also includes birds treated as described above with a superconcentrated preparation of exogenous antibody, i.e., antibody originating outside the bird.

DETAILED DESCRIPTION

It has been discovered that adequate amounts of antibody specific to a selected disease agent can be administered to birds to provide long-term disease protection. Antibody may be obtained from birds or mammals immunized against common poultry disease agents, including without limitation Newcastle disease virus and infectious bursal disease virus. The antibody is superconcentrated and is then passively provided to chicks by either the parenteral route of administration or by injecting eggs prior to hatching (in ovo injection). By "superconcentrated" is meant that the antibody has been concentrated to a titer of at least twice that present in the serum of an avian or mammalian animal immunized against the relevant disease agent. In the case of birds, a superconcentrated antibody preparation is one that has been concentrated such that the antibody titer is at least twice that obtainable, without concentration, from the yolk or serum. Preferably the antibody is concentrated to a titer at least about two to about five times that present in an unconcentrated serum or yolk immunoglobulin preparation. More preferably the antibody is concentrated to a titer at least about five to about ten times, and most preferably over about 10 times, that present in an unconcentrated serum or yolk immunoglobulin preparation. "Antibodies" as used herein includes whole antibodies of any class, i.e., IgG, IgA, IgM or any other known class. The term "antibodies" also includes portions or fragments of whole antibodies (e.g., Fab fragments) having specificity for the disease agent in question.

In one set of experiments, chicks were challenged with a virulent form of Newcastle disease virus every 2 weeks beginning at 1 week of age. Chicks that received a superconcentrated antibody preparation, by either subcutaneous administration or egg injection, were found to be protected from clinical disease (Newcastle disease) for periods beyond 7 weeks of age. The results demonstrated the protective effect of artificial passive immunity in preventing poultry diseases. Passive immunization also has been demonstrated for infectious bursal disease.

The methods of the invention surprisingly provide long-term passive protection from disease agents. To provide protection for the entire grow-out period of broiler chickens, for example, eggs or day-old hatchlings may be provided with superconcentrated antibody that affords protection over a period of more than about 4 weeks, if necessary beyond 7 weeks. Such long-term protection is not obtained following injection of antibody preparations having titers comparable to those found naturally in serum or yolk obtained from immunized birds or mammals.

Various procedures may be employed for purification and concentration of antibodies (IgG) from body fluids, including without limitation blood sera or plasma, egg yolk and ascites fluid. Suitable methods are described, for example, in McKinney et al., *J. Immunol. Methods* 96:271–78 (1987); Bhanushali et al., *Poultry Science* 73:1158–61 (1994), both references incorporated herein by reference.

In a preferred embodiment, chickens are immunized using standard procedures with the agent of choice, e.g. Newcastle disease virus, infectious bursal disease virus, infectious laryngotracheitis, infectious bronchitis, *Escherichia coli*, coccidia (Eimeria spp.) or other selected agents. Various known protocols may be used to immunize a bird. For example, an antigen, either live or inactivated, may be combined with an adjuvant and administered parenterally (e.g., subcutaneously) to a bird of any age, although an adult bird is preferred. Typically, volumes of 1–2 ml of vaccine preparation are injected at multiple sites, generally not exceeding 1 ml per site. The birds are revaccinated in the same way every 2–6 weeks to achieve a booster effect. This results in relatively high titer antisera or relatively high levels of antibodies in the yolk. The antibodies are harvested via blood collection and/or egg (yolk) collection.

Animals used as sources of antibodies may be immunized with more than one disease agent in order that the subsequently passively immunized birds are protected from a plurality of diseases. Alternatively, various antibody preparations, each having a specific and individual disease specificity, can be combined in order to provide a preparation having multiple disease specificities. In this latter case, the antibodies can be combined before, during, or after completion of the protocols for superconcentration described below.

Preferably, the collected antibodies are purified and concentrated by diluting with buffer, cooling, and acidifying with caprylic acid under cold conditions. Various acids may be substituted for caprylic acid. For example, phosphoric acid can be substituted for caprylic acid with satisfactory results. The preparation is centrifuged, generally at about 10,000×g for 30 minutes at 40° C., and the pelleted precipitate is discarded. The antibody is precipitated from the supernatant by ammonium sulfate precipitation. The preparation is again centrifuged and the precipitate is resuspended in buffer and dialysed against phosphate buffered saline (pH 7.2).

The resuspended antibody preparation is superconcentrated by lyophilizing using a commercial lyophilizer. The lyophilized antibody preparation can be stored for long periods without loss of activity. The lyophilized preparation is resuspended in sterile phosphate buffered saline (PBS) and diluted to the desired high ("Hi") titer. Preferably the lyophilized immunoglobulin is reconstituted in sterile phosphate-buffered saline (PBS) just prior to use. If necessary, antibiotics may be added to the diluent.

Generally, antibody preparations prepared as described above have Hemagglutination-Inhibition titers ranging between 1:32,768 to 1:131,072. Hemagglutination-Inhibition assays may be performed as described in Beard, C. W. Serologic Procedures. In: *Isolation and Identification of Avian Pathogens,* 3rd Ed., Purchase et al., eds., AAAP Publication, Kendall/Hunt Publ., Dubuque, Iowa, pages 192–200, 1989. A Hemagglutination-Inhibition was performed, for example, to determine the specific activity of Newcastle disease virus antibody, using 10 hemagglutination units (HA) of Newcastle disease virus as antigen.

Various alternatives to lyophilization may be used for superconcentrating the antibody preparation. Such alternative methods include without limitation drying, spray drying (for example as used to prepare powdered milk), and centrifugation methods. The superconcentrated antibody preparation can be administered by in ovo injection, preferably in volumes of 0.2 ml or less, of hatching eggs. In ovo injection may be accomplished manually or through use of commercial in ovo injection machines, for example the Inovoject® machines developed by Embrex, Inc., Research Triangle Park, N.C. The injectate (superconcentrated antibody in saline or other appropriate carrier solution) generally is administered below the egg's inner shell membrane into the aircell. In the case of chickens, this is typically done at the time the eggs are transferred from the incubator to the hatcher at approximately day 18 of incubation. Although the aircell is a preferred location for injection, it is to be understood that the injectate containing superconcentrated antibody can be administered to other locations in the egg. Alternatively the superconcentrated antibody preparation can be administered to day-old chicks by subcutaneous injection, preferably in a total injectate of no more than about 0.5 ml.

The methods of the invention can provide disease protection for at least the duration of the lifespan of a broiler chicken (4–8 weeks). As described above, antibody is superconcentrated and delivered to the bird in a small volume either by injecting the superconcentrated antibody under the skin or by injecting the superconcentrated antibody in the eggs prior to hatching. In either case, the passive protection engendered by superconcentrated antibody augments, as opposed to antagonizes, naturally occurring maternal antibody. The protection conveyed by the antibody is immediate, does not detract from any existing protection, does not induce stress or an active immune response in the bird and does not have the potential to perpetuate and/or generate new potential disease agents. The new approach permits disease protection without vaccine reaction. Such readily engendered passive immunity lends itself well to eradication programs by eliminating the use of live agents which may revert to virulent forms or recombine with virulent field strains (such is the case with infectious bursal disease).

The invention will be further understood with reference to the following illustrative embodiments, which are purely exemplary, and should not be taken as limiting the true scope of the present invention as described in the claims.

EXAMPLE 1

Representative Method for Superconcentrating Antibody

1. Take 50 ml of serum from a immunized animal.

2. Dilute serum with 200 ml of acetate buffer and adjust to pH 4.5.

3. Add 63 ml of caprylic acid, slowly and with constant stirring (25 $\mu$l caprylic acid/ml of diluted serum).

4. Stir 30 min.

5. Centrifuge at 10,000×g for 30 min. at 4° C.

6. Collect the supernatant and filter through a 0.45-$\mu$m nylon mesh (STRIVEX-HV 0.45 $\mu$m may be used with a peristaltic pump).

7. Mix the filtered supernatant with 1:10 its volume of 10×phosphate buffered saline (PBS) (i.e., 1 part 10×PBS to 10 parts supernatant) and adjust to pH 7.4 with 5N NaOH.

8. Slowly add 0.277g/ml of $(NH_4)_2SO_4$ to the resulting solution, while mixing. Preferably this is done at 4° C.

9. Mix for an additional 30 min. at 4° C.

10. Centrifuge at 10,000×g for 30 min. at 4° C.

11. Resuspend the pellet in a suitable volume of 1×PBS. For a starting volume of 50 ml serum as provided above, a suitable volume of 1×PBS is 5 ml.

12. Dialyze overnight against 1×PBS (50–100 volumes). Change the buffer at least twice.

The results of a typical run using the above procedures, for chickens immunized with Newcastle Disease virus, are presented below. Titers were determined by a Hemagglutination-Inhibition assay:

Beginning Volume: 50 ml

Beginning Titer: 1:2048

Final Volume: 8 ml

Final Titer: 1:4096–1:8192

EXAMPLE 2

Passive Protection Against Newcastle Disease Virus

Groups of specific pathogen free (SPF, Hyvac®) chicks were inoculated subcutaneously at one day of age with 0.5 ml of superconcentrated antibody, prepared as described in Example 1, above. In the experiments summarized in the tables below, negative control sera had Hemagglutination-Inhibition titers of less than 1:2, low titer antibody preparations (Lo titer) had Hemagglutination-Inhibition titers of about 1:32, and superconcentrated antibody preparations (Hi titer) had Hemagglutination-Inhibition titers of about 1:8, 192. As used below, the term "$EID_{50}$" means "egg infectious dose, 50%," that is, the dose of disease agent at which 50% of the eggs become infected. At various weeks of age, the birds were challenged with $10^4 EID_{50}$ of the Texas GB (TxGB) strain of velogenic Newcastle Disease virus, obtained from the National Veterinary Services Laboratory, Ames, Iowa. The challenge virus was administered by the intraocular/intranasal route. One drop (0.1 ml) of virus preparation was instilled directly into the eye and one drop (0.1 ml) was instilled directly into the nares.

Results of these experiments are summarized in the tables below.

TABLE 1

Results of passively immunizing specific pathogen free (SPF) chicks with superconcentrated antibody directed against Newcastle disease virus.

| Group[A] | Chall Wk[B] | N | Prechall[C] GMT | Prot[D] | % Prot |
|---|---|---|---|---|---|
| Cont.-Neg. Inocula | —[E] | 5 | 0.4 | — | — |
| Lo Titer Inocula | — | 5 | 2.2 | — | — |
| Hi Titer Inocula | — | 5 | 8.8 | — | — |
| Cont.-Neg. Inocula | 1 | 20 | 0.45 | 0/20 | 0% |
| Lo Titer Inocula | 1 | 20 | 1.35 | 0/20 | 0% |
| Hi Titer Inocula | 1 | 20 | 8.26 | 20/20 | 100% |
| Cont.-Neg. Inocula | 3 | 20 | 0.8 | 0/20 | 0% |
| Lo Titer Inocula | 3 | 20 | 1.8 | 0/20 | 0% |
| Hi Titer Inocula | 3 | 20 | 4.9 | 20/20 | 100% |
| Cont.-Neg. Inocula | 5 | 20 | 0.3 | 0/20 | 0% |
| Lo Titer Inocula | 5 | 20 | 0.25 | 0/20 | 0% |
| Hi Titer Inocula | 5 | 20 | 2.75 | 20/20 | 100% |
| Cont.-Neg. Inocula | 7 | 15 | 0 | 4/15 | 27% |
| Lo Titer Inocula | 7 | 13 | 0.15 | 0/13 | 0% |
| Hi Titer Inocula | 7 | 14 | 1.4 | 14/15 | 93% |

[A]Groups of SPF chicks inoculated subcutaneously at one day of age with 0.5 ml of antibody preparation. Hemagglutination-Inhibition titers of Negative Control Sera were < 1:2, of Low Titer = 1:32 and of Hi Titer = 1:8, 192
[B]Weeks of age that birds were challenged with $10^4$ $EID_{50}$ of TxGB challenge virus by the intraocular/intranasal route
[C]Prechallenge geometric mean titer (GMT) of group (n), displayed as reciprocal Log2
[D]Protection = number of birds NOT displaying clinical signs of disease (or death) per number of birds challenged
[E]Blood samples taken at 2 days of age The results of a second series of similar experiments are provided in Table 2, below.

TABLE 2

Results of passively immunizing specific pathogen free (SPF) chicks or eggs with superconcentrated antibody directed against Newcastle disease virus.

| Group[A] | Chall Wk[B] | N | Prechall[C] GMT | Prot[D] | % Prot |
|---|---|---|---|---|---|
| In ovo-Neg. sera | —[E] | 5 | 1.0 | — | — |
| In ovo-Hi titer | — | 5 | 6.6 | — | — |
| In ovo-PBS | — | 5 | 0.8 | — | — |
| Day-old-Neg. sera | — | 5 | 1.0 | — | — |
| Day-old-Hi titer | — | 5 | 7.6 | — | — |
| In ovo-Neg. sera | 1 | 15 | 0.3 | 0/15 | 0% |
| In ovo-Hi titer | 1 | 15 | 5.8 | 14/15 | 93% |
| In ovo-PBS | 1 | 15 | 0.6 | 0/15 | 0% |
| Day-old-Neg. sera | 1 | 17 | 0.4 | 0/17 | 0% |
| Day-old-Hi titer | 1 | 17 | 6.7 | 16/17 | 94% |
| In ovo-Neg. sera | 3 | 18 | 0.9 | 0/18 | 0% |
| In ovo-Hi titer | 3 | 15 | 3.1 | 13/15 | 87% |
| In ovo-PBS | 3 | 15 | 0.9 | 0/15 | 0% |
| Day-old-Neg. sera | 3 | 19 | 0.7 | 0/19 | 0% |
| Day-old-Hi titer | 3 | 20 | 3.7 | 19/20 | 95% |
| In ovo-Neg. sera | 5 | 20 | 0.9 | 1/20 | 5% |
| In ovo-Hi titer | 5 | 17 | 2.0 | 13/17 | 76% |
| In ovo-PBS | 5 | 18 | 0.0 | 0/18 | 0% |
| Day-old-Neg. sera | 5 | 19 | 0.9 | 1/19 | 5% |
| Day-old-Hi titer | 5 | 20 | 2.7 | 19/20 | 95% |
| In ovo-Neg. sera | 7 | 20 | 0 | 2/20 | 10% |
| In ovo-Hi titer | 7 | 17 | 0.53 | 9/17 | 53% |
| In ovo-PBS | 7 | 19 | 0 | 2/19 | 11% |
| Day-old-Neg. sera | 7 | 19 | 0 | 0/19 | 0% |
| Day-old-Hi titer | 7 | 20 | 0.3 | 17/20 | 85% |
| In ovo-Neg. sera | 9 | 20 | 0.6 | 6/20 | 30% |
| In ovo-Hi titer | 9 | 17 | 0.0 | 7/17 | 41% |
| In ovo-PBS | 9 | 19 | 0.1 | 3/19 | 16% |
| Day-old-Neg. sera | 9 | 17 | 1.0 | 5/17 | 29% |
| Day-old-Hi titer | 9 | 20 | 0.0 | 10/20 | 50% |

[A]Groups of SPF chicks inoculated subcutaneously at one day of age, or chicks hatched from eggs injected in ovo, with 0.2 ml of inocula. Hemagglutination-Inhibition titers of Negative Control Sera were < 1:2, of Hi Titer = 1:8, 192
[B]Weeks of age that birds were challenged with $10^4$ $EID_{50}$ of TxGB challenge virus by the intraocular/intranasal route
[C]Prechallenge geometric mean titer of group (n), displayed as reciprocal Log2
[D]Protection = number of birds NOT displaying clinical signs of disease (or death) per number of birds challenged
[E]Blood samples taken at 2 days of age In another series of experiments, Hemagglutination-Inhibition titers of post-hatch birds at 0–9 weeks of age were measured following injection of eggs with superconcentrated antibody specific for Newcastle Disease virus. The results are set out in Table 3, below.

TABLE 3

Postinoculation titers of birds hatched from in ovo injected eggs

| Group | Inocula | N | Inocula Amt | 0 | 1 | 2 | 3 | 4 | 5 | 6 | 7 | 8 | 9 |
|---|---|---|---|---|---|---|---|---|---|---|---|---|---|
| 1 | Neg. Sera | 6 | 0.2 ml | 0 | ND[B] | 0 | 0 | ND | ND | ND | ND | ND | ND |
| 2 | Hi Titer Sera[A] | 5 | 0.1 ml | 5.8 | 5.6 | 4.4 | 3.0 | 2.8 | 1.6 | 1 | 0.8 | 0.3 | 0 |
| 3 | Hi Titer Sera[A] | 5 | 0.2 ml | 6.0 | 7.8 | 6.8 | 5.0 | 4.6 | 3.2 | 2.4 | 1.8 | 1.2 | 0.3 |

[A]Hemagglutination-Inhibition Titer of 1:65, 536
[B]ND = Not Done

The data set out above demonstrate that superconcentrated antibody is capable of providing long-term passive protection from Newcastle Disease Virus.

EXAMPLE 3

Passive Protection Against Infectious Bursal Disease (IBD)

Three-week-old specific pathogen free (SPF, Hyvac®) chickens were used in experiments designed to demonstrate that superconcentrated antibody preparations of anti-infectious bursal disease virus antibodies could protect susceptible birds from challenge with virulent IBD virus (IBDV). The standard challenge strain (STC) of IBDV was obtained from the National Veterinary Services Laboratory (NVSL, Ames, Iowa). The virus titer was provided by the NVSL at $10^{4.1}$ $EID_{50}$. The virus was administered both intraocularly and orally in a total volume of 0.1 ml/bird containing $10^2 EID_{50}$.

Hyperimmune sera were collected from adult SPF birds vaccinated with commercially prepared killed adjuvanated IBD vaccine (Bursine®-KACL™, Solvay Animal Health, Inc.). The sera were pooled and concentrated by the methods described in Example 1, above. The preconcentration titer of the hyperimmune pooled sera was 1:25,600 as measured with an avidin-biotin enhanced dot-immunobinding assay (ELISA titer, DAB assay; Cummins et al., *Avian Dis.* 34: 36–43 (1990)). The postconcentration titer of the superconcentrated antibody preparation was 1:204,800, as measured by the ELISA titer, DAB assay.

Three groups of three-week-old SPF birds were used as follows: group 1: unvaccinated, unchallenged control birds; group 2: unvaccinated, challenged birds; group 3: passively immunized (with the superconcentrated antibodies), challenged birds. Birds in group 3 were passively immunized by subcutaneous administration of 1.0 ml of a superconcentrated antibody preparation two days prior to challenge. Blood samples were taken from birds in all groups immediately prior to challenge for assessment of prechallenge IBD antibody titers. Birds were observed for a two week challenge period. At 14 days postchallenge, birds were necropsied and body weights, bursa weights and bursa-to-body weight ratios (BBR) were determined.

No clinical signs of disease were observed in any birds throughout the duration of the trial. Further results are provided in Table 4, below.

TABLE 4

| Group | N | Prechall Titer | Ave. Bod. Wgt. | Ave. Bursal Wgt. | Ave. BBR |
|---|---|---|---|---|---|
| #1-Neg. Controls | 8 | Neg. | 439 | 2.14 | 0.48 |
| #2-Challenge | 8 | Neg. | 409 | 0.43$^A$ | 0.11$^A$ |
| #3-Pass Immun & Chall | 4 | 4.3$^B$ | 473 | 2.23 | 0.47 |

$^A$Statistically different from other groups within the column (P < 0.001, by t-test & Tukey method)
$^B$Geometric mean titer expressed as reciprocal Log2 × 100 (i.e. 1:1970)

From these results, it is concluded that superconcentrated anti-IBDV antibody is capable of protecting birds from virulent challenge.

What is claimed is:

1. A method of providing artificial passive immunity to a disease agent that engenders natural passive immunity in an avian species, comprising administering a preparation of superconcentrated avian antibody to an egg of said species, said avian antibody administered in an amount effective to provide, to a bird derived from said egg, long-term passive protection from said disease agent.

2. The method of claim 1, wherein said disease agent is selected from the group consisting of Newcastle disease virus and infectious bursal disease virus.

3. The method of claim 1, wherein said species is *Gallus gallus*.

4. The method of claim 3, wherein said egg is to be used for production of a broiler chicken.

5. The method of claim 1, wherein said long-term passive protection is for a period of at least 5 weeks.

6. The method of claim 1, wherein said long-term passive protection is for a period of at least 7 weeks.

7. The method of claim 1, wherein said preparation is concentrated to an antibody titer at least about 5 times that present in an unconcentrated serum or yolk immunoglobulin preparation.

8. The method of claim 1, wherein said preparation is concentrated to an antibody titer at least about 10 times that present in an unconcentrated serum or yolk immunoglobulin preparation.

9. A method of providing artificial passive immunity to a disease agent that engenders natural passive immunity in an avian species to a bird, comprising parenteral administration of a preparation of superconcentrated avian antibody to said bird, said preparation administered in an amount effective to provide passive protection to said bird for a period greater than four weeks, from said disease agent.

10. The method of claim 9, wherein said disease agent is selected from the group consisting of Newcastle disease virus and infectious bursal disease virus.

11. The method of claim 9, wherein said species is *Gallus gallus*.

12. The method of claim 11, wherein said bird is a hatchling to be used for production of a broiler chicken.

13. The method of claim 9, wherein said preparation of superconcentrated avian antibody is administered by subcutaneous injection.

14. The method of claim 9, wherein said period of passive protection is for at least 5 weeks.

15. The method of claim 9, wherein said period of passive protection is for at least 7 weeks.

16. The method of claim 9, wherein said preparation is concentrated to an antibody titer at least about 5 times that present in an unconcentrated serum or yolk immunoglobulin preparation.

17. The method of claim 9, wherein said preparation is concentrated to an antibody titer at least about 10 times that present in an unconcentrated serum or yolk immunoglobulin preparation.

* * * * *